(12) United States Patent
Nobles et al.

(10) Patent No.: US 11,787,063 B2
(45) Date of Patent: Oct. 17, 2023

(54) LINEAR LOCK AND ADJUSTABLE ARM SUPPORT SYSTEM

(71) Applicant: Verb Surgical Inc., Santa Clara, CA (US)

(72) Inventors: Brent Michael Nobles, Durham, NC (US); Joan Savall, Palo Alto, CA (US); Scott Anderson, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 350 days.

(21) Appl. No.: 17/018,277

(22) Filed: Sep. 11, 2020

(65) Prior Publication Data

US 2022/0080602 A1 Mar. 17, 2022

(51) Int. Cl.
| | |
|---|---|
| *A47C 7/54* | (2006.01) |
| *A47C 1/03* | (2006.01) |
| *B25J 13/06* | (2006.01) |
| *B25J 9/16* | (2006.01) |
| *A61G 15/12* | (2006.01) |
| *A61B 90/60* | (2016.01) |
| *A61B 34/35* | (2016.01) |
| *A61B 34/30* | (2016.01) |

(52) U.S. Cl.
CPC ............. *B25J 13/06* (2013.01); *A47C 7/543* (2013.01); *A61B 34/35* (2016.02); *A61B 90/60* (2016.02); *A61G 15/12* (2013.01); *B25J 9/1689* (2013.01); *A61B 2034/301* (2016.02)

(58) Field of Classification Search
CPC ..... A47C 1/0307; A47C 1/0308; A47C 7/543; A61B 34/35; A61B 90/60; A61B 2034/301; A61G 15/12; B25J 13/06; B25J 9/1689
See application file for complete search history.

(56) References Cited

U.S. PATENT DOCUMENTS

| | | | | |
|---|---|---|---|---|
| 5,380,065 | A * | 1/1995 | Rohrer | A47C 1/0308 297/411.37 |
| 5,590,934 | A * | 1/1997 | Gibbs | A47C 1/03 297/411.37 |
| 5,651,586 | A * | 7/1997 | Groth | A47C 1/0307 297/411.31 |
| 5,655,814 | A * | 8/1997 | Gibbs | A47C 1/03 248/118 |
| 5,733,010 | A | 3/1998 | Lewis et al. | |
| 5,752,683 | A * | 5/1998 | Novis | A47C 1/0307 297/411.36 X |
| 5,851,054 | A | 12/1998 | Bergsten et al. | |
| 5,876,097 | A * | 3/1999 | Cao | A47C 1/03 297/411.37 |

(Continued)

FOREIGN PATENT DOCUMENTS

| | | | | |
|---|---|---|---|---|
| FR | | 2748919 A1 * | 11/1997 | ............ A47C 1/03 |
| WO | WO2002015749 B1 | | 7/2002 | |

(Continued)

*Primary Examiner* — Rodney B White
(74) *Attorney, Agent, or Firm* — Aikin & Gallant, LLP

(57) ABSTRACT

An adjustable arm support for a surgical robotic system, the arm support comprising: a fixed armrest portion that is fixedly coupled to a console seat of the surgical robotic system; and an adjustable armrest portion that is adjustably coupled to the fixed armrest portion, the adjustable armrest portion.

20 Claims, 11 Drawing Sheets

(56) References Cited

U.S. PATENT DOCUMENTS

| | | | |
|---|---|---|---|
| 5,927,811 A * | 7/1999 | Tseng | A47C 1/03 297/411.31 |
| 5,975,640 A * | 11/1999 | Chen | A47C 1/03 297/411.31 |
| 6,017,091 A * | 1/2000 | Cao | A47C 1/03 297/411.37 |
| 6,076,891 A * | 6/2000 | Bernhardt | A47C 7/541 297/411.31 |
| 6,213,556 B1 * | 4/2001 | Chen | A47C 1/03 297/411.37 |
| 6,460,932 B1 * | 10/2002 | Kopish | A47C 1/03 297/411.36 |
| 6,520,587 B2 | 2/2003 | Noiseux | |
| 6,619,747 B2 | 9/2003 | Ko et al. | |
| 6,916,068 B2 | 7/2005 | Kitamura et al. | |
| 6,948,774 B2 * | 9/2005 | Maier | A47C 1/03 297/411.31 |
| 6,948,775 B2 * | 9/2005 | Tsai | A47C 1/03 297/411.37 |
| 7,004,546 B1 | 2/2006 | Thisius et al. | |
| 7,150,504 B1 * | 12/2006 | Lee | A47C 1/0307 297/411.35 |
| 7,159,947 B1 * | 1/2007 | Lee | A47C 1/0308 297/411.37 |
| 7,201,449 B2 * | 4/2007 | Tsai | A47C 1/0308 297/411.36 |
| 7,234,779 B2 * | 6/2007 | Bedford | A47C 1/03 297/411.36 |
| 7,387,341 B1 * | 6/2008 | Tsai | A47C 1/0307 297/411.37 |
| 7,452,032 B1 | 11/2008 | Roleder et al. | |
| 8,480,172 B2 | 7/2013 | Baker | |
| 8,496,295 B2 * | 7/2013 | Chen | A47C 1/03 297/411.31 |
| 8,596,716 B1 * | 12/2013 | Caruso | B60N 2/0228 297/217.3 |
| 8,944,511 B2 | 2/2015 | Wang | |
| 8,967,724 B2 * | 3/2015 | Battey | A47C 31/023 297/411.36 |
| 9,028,001 B2 | 5/2015 | Battey et al. | |
| 9,155,395 B2 | 10/2015 | Hair et al. | |
| 9,320,360 B2 * | 4/2016 | Bauer | A47C 1/03 |
| 9,345,333 B2 | 5/2016 | Gorgi | |
| 9,415,710 B2 | 8/2016 | Simon et al. | |
| 9,427,085 B2 | 8/2016 | Battey et al. | |
| 9,700,139 B2 * | 7/2017 | Su | A47C 1/0308 |
| 9,872,565 B2 | 1/2018 | Battey et al. | |
| 9,907,403 B2 | 3/2018 | Lin et al. | |
| 10,433,646 B1 * | 10/2019 | Schmidt | A47C 1/143 |
| 10,537,176 B2 * | 1/2020 | Bock | A47C 1/0303 |
| 10,674,827 B2 * | 6/2020 | Chen | A47C 7/38 |
| 10,786,082 B1 * | 9/2020 | Lai | A47C 1/0308 |
| 11,089,876 B2 * | 8/2021 | Chen | A47C 7/541 |
| 11,266,247 B2 * | 3/2022 | Chen | A47C 7/546 |
| 11,324,326 B2 * | 5/2022 | Hsieh | A47C 1/0305 |
| 11,337,527 B2 * | 5/2022 | Chen | A47C 1/0307 |
| 2002/0135210 A1 | 9/2002 | Tseng | |
| 2003/0030317 A1 * | 2/2003 | Chen | A47C 1/03 297/411.35 |
| 2004/0135419 A1 | 7/2004 | Kitamura et al. | |
| 2005/0116519 A1 | 6/2005 | Wullum | |
| 2006/0238011 A1 * | 10/2006 | Bedford | A47C 1/0308 297/411.35 |
| 2007/0096531 A1 | 5/2007 | Bruns et al. | |
| 2008/0073965 A1 * | 3/2008 | Tsai | A47C 1/0307 297/411.36 |
| 2008/0138149 A1 | 6/2008 | Selbekk et al. | |
| 2008/0309141 A1 * | 12/2008 | Michael | A47C 1/03 297/411.36 |
| 2009/0033139 A1 * | 2/2009 | Michael | A47C 1/03 297/411.37 |
| 2011/0163577 A1 | 7/2011 | Anastasov | |
| 2012/0175934 A1 * | 7/2012 | Bock | A47C 1/0307 297/411.37 |
| 2014/0077566 A1 | 3/2014 | Battey et al. | |
| 2014/0077572 A1 * | 3/2014 | Vander Veen | A47C 7/24 297/452.1 |
| 2014/0145490 A1 * | 5/2014 | Chen | A47C 1/03 297/411.37 |
| 2014/0217798 A1 | 8/2014 | Negusse | |
| 2015/0298587 A1 * | 10/2015 | Michael | B60N 2/78 297/411.38 X |
| 2016/0183687 A1 * | 6/2016 | Hoyt | A47C 7/56 297/217.2 |
| 2016/0286965 A1 * | 10/2016 | Koch | A47C 7/748 |
| 2016/0324320 A1 | 11/2016 | Battey et al. | |
| 2017/0112289 A1 * | 4/2017 | Wickett | A47C 7/563 |
| 2018/0103759 A1 | 4/2018 | Battey et al. | |
| 2020/0345142 A1 * | 11/2020 | Battey | A47C 1/0308 |
| 2021/0145670 A1 * | 5/2021 | Son | A61G 5/1067 |
| 2021/0197095 A1 * | 7/2021 | Menard | H04N 21/4222 |
| 2021/0219729 A1 * | 7/2021 | Bock | A47C 7/541 |

FOREIGN PATENT DOCUMENTS

| | | |
|---|---|---|
| WO | WO2006001701 A1 | 1/2006 |
| WO | WO2007115418 A2 | 10/2007 |

* cited by examiner

LINEAR LOCK AND ADJUSTABLE ARM SUPPORT SYSTEM

BACKGROUND

Field

Embodiments related to an adjustable arm support for surgical robotic systems, are disclosed. More particularly, embodiments related to a linear and pivotally adjustable arm support for surgical robotic systems which includes a locking mechanism, are disclosed.

Background

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

The robotic systems may be remotely operated by a surgeon to command the robotically-assisted arms and/or tools located at an operating table. Such operation of a robotically-assisted tool remotely by a surgeon may be commonly referred to as teleoperation. For example, the surgeon may use a computer console located at a surgeon bridge in the operating room, or it may be located in a different city, to command a robot to manipulate the surgical tool mounted on the operating table. The robotically-controlled surgical tool can be, for example, an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in his or her hand a user input device such as a controller that he/she manipulates to generate control signals to cause motion of the surgical robotic system components, e.g., an actuator, a robotic arm, and/or a surgical tool of the robotic system.

SUMMARY

During a remote surgical procedure, the surgeon may use a user input device (UID), for example an ungrounded hand held controller, at the surgeon bridge for up to several hours. The surgeon must be able to perform precise movements and limit fatigue. The surgeon bridge or console may therefore include an arm support system (e.g., an armrest) that can support the surgeon's arm while they are holding the UID and performing the surgical procedures. The arm support system (armrest) must accommodate a variety of user sizes in all positions supported by the surgeon bridge (seated, reclined and elevated). The armrest may be adjustable to accommodate the different user sizes and variety of uses. In one aspect, the armrest may allow for two types of adjustment: linear (to adjust for depth) and rotational (to adjust the angle) in relation to the user (arm positioning, conforming to user size). For example, the arm support system may include adjustments that allow the user to enter from the front of the seat, allow for quick egress/ingress and not interfere with the overall width of the system or other elements of the system like the open display. In addition, the linear adjustment mechanism and/or the rotational adjustment mechanism may allow for distinct positioning between storage and use positions, as well as simple adjustment for user size and position of the armrest around the surgeon. In addition, the system may have a distinct area for teleoperation (work surface), user input areas (buttons/touch input) and comfort/egress support.

The armrests may also have distinct surfaces that can be used to indicate and physically direct the user to specific positioning, for example positions in front of the body, that reduce fatigue, increase precision or stay within a particular workspace. In some cases, the armrests may have work and/or support surfaces that can be positioned in front of the user. The work and/or support surfaces may be used to support the user's forearms/elbows/wrists during teleoperation with the ungrounded controllers. Representatively, an adjustable portion of the armrest may be used to set the size of the workspace and direct the user to position their arms in preferred positions for teleoperation. For example, the width/gap between arms or other geometry of the armrest support surface in front of the user may be used to direct the user to positions that have been shown to be more ergonomic or provide better results for long term use, fatigue reduction, precise movements etc. The surfaces may also be used to indicate the workspace size for applications using ungrounded UIDs. The adjustable portion of the armrests can also be used to set the support surface and/or indicate either the width or depth of the workspace. In some aspects, the top surface of the adjustable armrest portion may be the work surface, as opposed to the static portion of the armrest which may have a wider stance that reduces range of motion and may be outside of the workspace. This is further indicated by distinct levels for the work surface of the adjustable armrest portion and comfort/support surfaces of the fixed armrest portion.

There are many possible shapes of the deployment arm that facilitate use of work surfaces depending on the type of work being done. For example: a rounded or angled edge opposite of the user in the adjustable armrest portion can be used to angle the users arms downward maximize range of use and positioning for ergonomic and precise movements of the UIDs.

In addition, the system may include a deployment adjustment joint mechanism to facilitate consistent and even adjustment of the armrest (or deployment arm). The mechanism may allow for tunable holding force, and specific angles of adjustment without electronic inputs or extra steps by the user to set the position. Representatively, the joint mechanism may include a cam profile and detents that allow for distinct locations of adjustments in specific ranges useful to the user.

Representatively, in one aspect an adjustable arm support for a surgical robotic system includes a fixed armrest portion that is fixedly coupled to a console seat of the surgical robotic system; and an adjustable armrest portion that is movably coupled to the fixed armrest portion, the adjustable armrest portion is operable to be adjusted linearly and rotatably relative to the fixed armrest portion. The adjustable armrest portion may be linearly adjusted between a stored position and a deployed position. For example, the adjustable armrest portion may include a linear slide that translates along a linear rail coupled to the fixed armrest portion to allow for adjustment of the adjustable armrest portion between the stored position and the deployed position. In some aspects, the adjustable armrest portion may include a proximal end and a distal end and the distal end is adjacent the fixed armrest portion in the stored position and distal to the fixed armrest portion in the deployed position. The adjustable armrest portion may further be rotatably adjusted between a stored position and a deployed position. The adjustable armrest portion may run parallel to the fixed armrest portion in the stored position and may be at an angle to the fixed armrest portion in the deployed position. In still further aspects, the fixed armrest portion may include a support surface and the adjustable armrest portion may include a work surface that is out-of-plane relative to the support surface. In addition, the armrest may include a linear locking mechanism that prevents a linear adjustment of the adjustable armrest portion relative to the fixed armrest portion upon application of a downward force to the adjustable armrest portion. The armrest may further include a rotational locking mechanism for adjusting a force required for a rotational adjustment of the adjustable armrest portion relative to the fixed armrest portion. The rotational locking mechanism may include a cam having at least one notch and at least one detent that engages with the at least one notch to increase the force required for rotational adjustment.

In another aspect, an adjustable arm support for a surgical robotic system may include an armrest base that is fixedly coupled to a user console seat of the surgical robotic system; a deployment arm coupled to the armrest base, the deployment arm is operable to be linearly or rotatably adjusted relative to the armrest base between a stored position and a deployed position; and a locking mechanism operable to lock the deployment arm in the deployed position by preventing a linear or rotatable adjustment of the deployment arm relative to the armrest base. In some aspects, in the stored position, the deployment arm is parallel to the armrest base. In still further aspects, in the deployed position, the deployment arm is at an angle up to 90 degrees relative to the armrest base. The locking mechanism may include a linear locking mechanism that prevents a linear adjustment of the deployment arm upon application of a downward force to the deployment arm. The linear locking mechanism may include a channel within the armrest base that engages with a sliding member of the deployment arm upon application of the downward force to the deployment arm to prevent the linear adjustment. The locking mechanism may also include a rotational locking mechanism that adjusts a force required for a rotatable adjustment of the deployment arm. The rotational locking mechanism may include a cam with at least one notch coupled to the deployment arm and at least one detent coupled to the armrest base, and the at least one detent may engage the at least one notch to increase the force required for rotatable adjustment of the deployment arm. The cam may include at least two notches and at least two detents are coupled to the armrest base, and engaging the at least two detents with the at least two notices increases a force required to rotate the deployment arm. In some aspects, the at least one detent is coupled to a spring that biases the at least one detent toward the at least one notch. In addition, the rotational locking mechanism may provide a haptic feedback to a user when the deployment arm is rotatably adjusted relative to the armrest base between the stored position and the deployed position.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
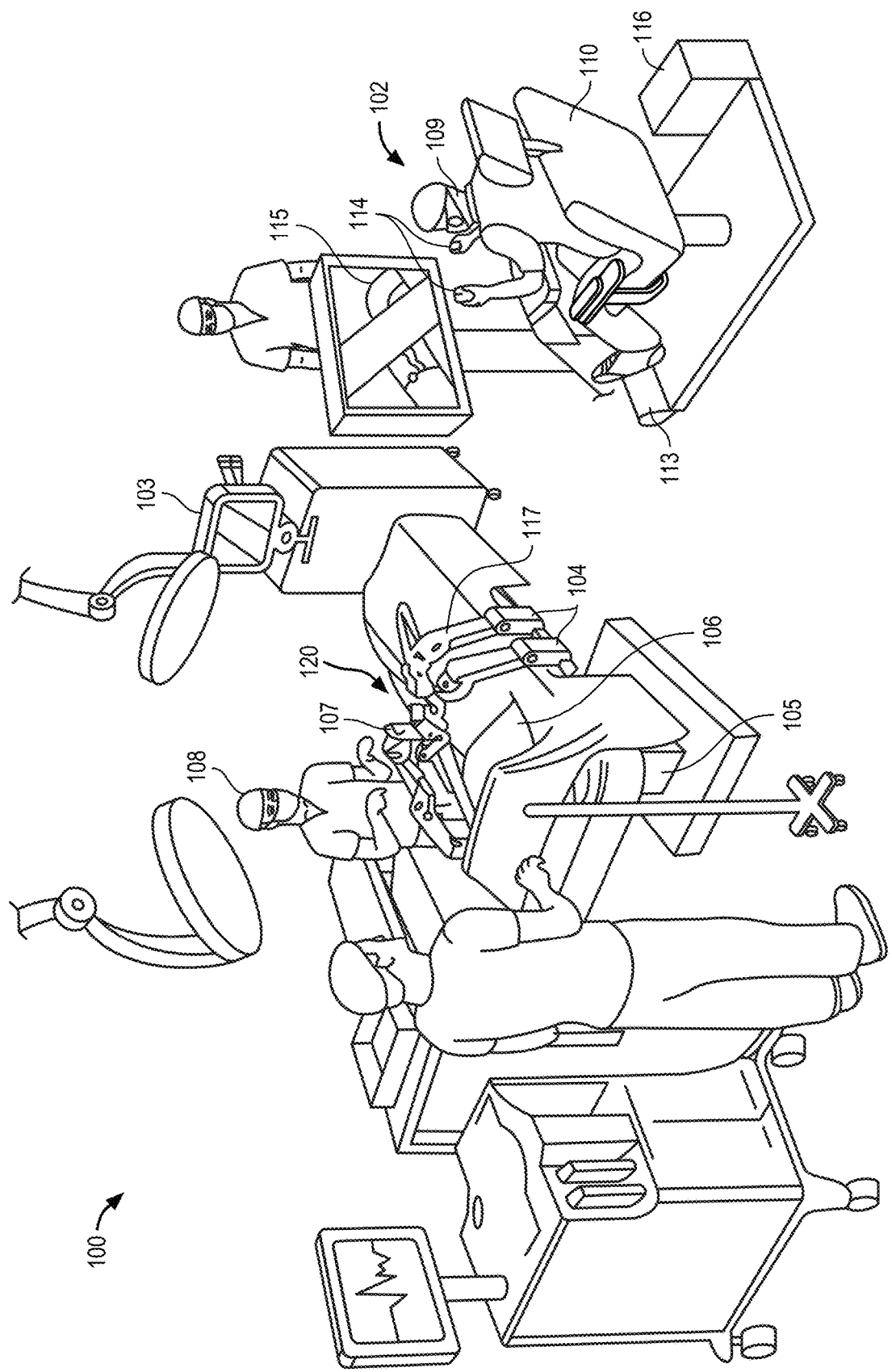
FIG. 1 is a pictorial view of an example surgical robotic system in an operating arena.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may include a chair or seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilisation and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. When the user is finished controlling the surgical tools with the UIDs 114, the user may dock (i.e., store) the UIDs 114 with docking stations or UID holders located on the console 102. For example, the console 102 may include docking stations 130 at each of the left and right armrests of the seat 110. To dock the UIDs 114, the user may move the left UID 114 to the left docking station 130 and the right UID 114 to the right docking station 130, and place each UID in their respective docking station holder.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

In addition, in some aspects, surgical robotic system 100 may further include one or more tracking mechanisms, devices, components or systems (e.g., trackers, sensors, etc), that can be used to detect one or more actions of the surgical system components and/or the surgeon. The mechanisms may detect, for example, a movement of the user's head relative to the display 115 or a movement of a UID being held by the user. This information may, in turn, be used to determine whether the movement indicates the user intends to disengage/engage teleoperation mode (e.g., a pre-disengagement action) or continue engagement of a teleoperation mode (e.g, a pre-engagement action). It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that a detected movement is an unintended action or movement by the user.

Figure 2:
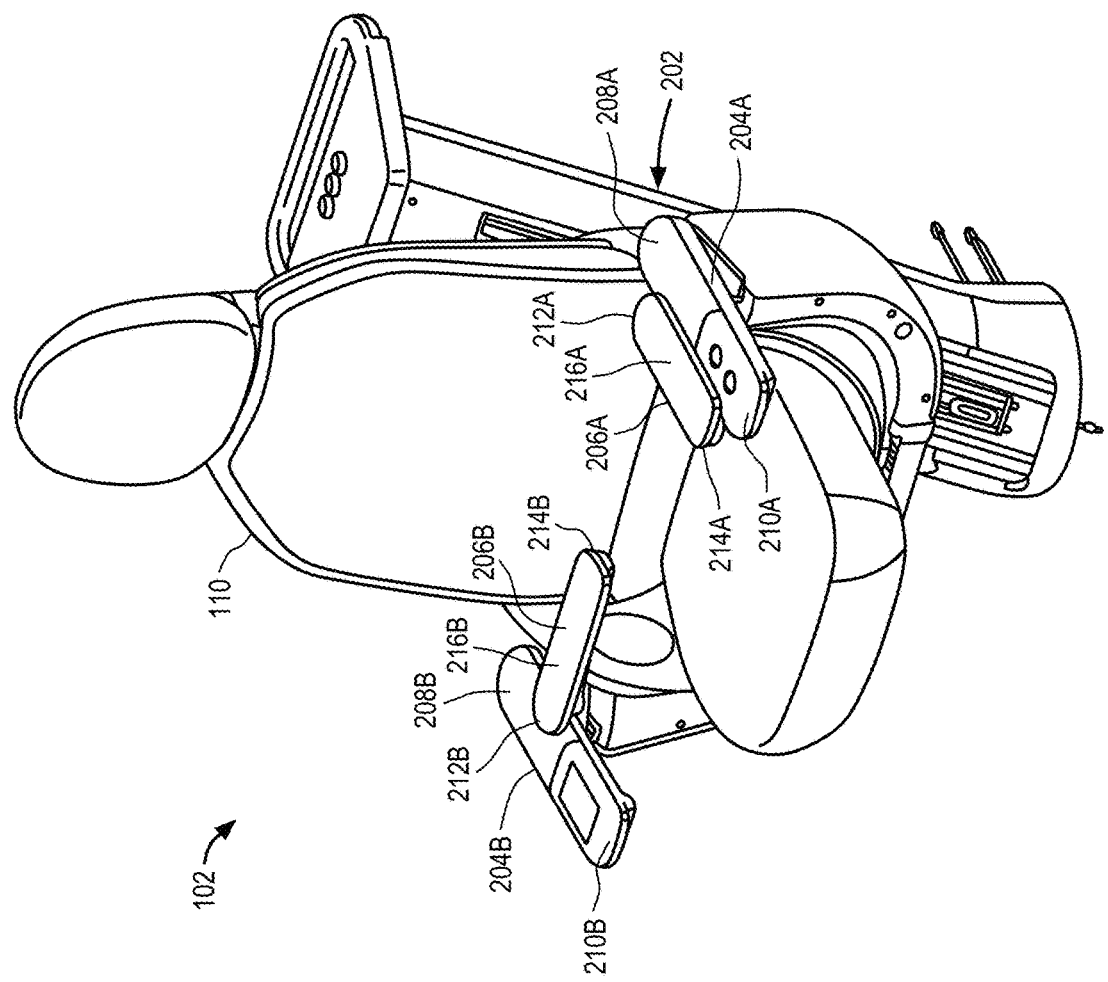
FIG. 2 illustrates a perspective view of an exemplary user console seat including an adjustable armrest system.

Referring now to FIG. 2, FIG. 2 illustrates a side perspective view of an exemplary user console including a seat with an adjustable arm support system. Representatively, user console 102 is shown including a seat 110 and adjustable arm support system 202 attached to the seat 110. The adjustable arm support system 202 may include left and right fixed arm support or armrest portions 204A, 204B that may be fixedly attached (e.g., mounted) to the seat 110. The adjustable arm support system 202 may further include left and right adjustable arm support or armrest portions 206A, 206B that may be movably attached to the fixed armrest portions 204A, 204B, respectively. The adjustable armrest portions 206A-B may be both linearly and rotatably moved relative to the fixed armrest portions 204A-B. The adjustable armrest portions 206A and the adjustable armrest portion 206B may be independently moved such that the movements are the same or different and/or may be at the same or different times. The particular arrangement and movement of the adjustable armrest portions 206A-B relative to the fixed armrest portions 204A-B will be described in more detail in reference to FIGS. 3-11.

Referring now in more detail to the fixed armrest portion 204A-B, the fixed armrest portion 204A-B may be an elongated structure (e.g., rectangular, elliptical or the like) that does not move relative to seat 110 and is mounted to the seat 110 in a fixed orientation. The fixed armrest portion 204A-B may serve as the base portion for the entire armrest structure and may therefore also be referred to herein as an armrest base. The fixed armrest portion 204A-B may include a support surface 208A, 208B at an end (e.g, a proximal end) attached to the seat 110. The support surface 208A-B may be near the back of the seat 110 (e.g., seat portions supporting the user's back) such that this portion provides support for a portion of the user's arm closest to the seat back, or closest to the user's body. The other end (e.g., a distal end) of the fixed armrest portion 204A-B may include an input surface 210A, 210B. The input surface 210A-B may include buttons, touch input mechanisms or the like and be near the front end of the seat 110 such that the user can input commands into the input surface 210A-B with their hands.

The adjustable armrest portion 206A-B may also be an elongated structure but may be shorter than the fixed armrest portion 204A-B. The adjustable armrest portion 206A-B may have a shape and/or size that facilitates use of its work surface based on the type of operation being performed by the user. For example, the adjustable armrest portion 206A-B may have a rounded or angled edge opposite the user such that when in the deployed position (e.g., the position of armrest portion 206B shown in FIG. 2), it can be used to angle the user's arms downward to maximize range of use and positioning for ergonomic and precise movements of the UID. The adjustable armrest portion 206A-B may have a proximal end 212A, 212B movably attached to the fixed armrest portion 204A-B and a distal end 214A, 214B. The proximal end 212A-B may slide, rotate and/or pivot relative to the fixed armrest portion 204A-B, which in turn slides, rotates and/or pivots the distal end 214A-B. The proximal end 212A-B may, in some embodiments, be directly attached to the fixed armrest portion 204A-B. The distal end 214A-B may be considered a free end because it is not directly attached to the fixed armrest portion 204A-B. The top surface of the adjustable armrest portion 206A-B may define a work surface 216A-B that is configured to support the surgeon's wrist, forearm and/or elbow to rest on during a surgical procedure using the UIDs.

In some aspects, the work surface 216A-B may be at a higher level than, or otherwise out-of-plane relative to, the support surface 208A-B and input surface 210A-B of the fixed armrest portion 204A-B. In this aspect, the work surface 216A-B and surfaces 208A-B, 210A-B are distinct and can be used to guide the use of the system. For example, the different surfaces can indicate and physically direct the user to specific armrest positions that may reduce fatigue, increase precision and/or help the user stay within a particular workspace. Representatively, the work surface 216A-B and surfaces 208A-B, 210A-B may be used to set the size of the workspace and direct the user to position their arms in a preferred position for teleoperation. In other aspects, the width/gap between the armrest portion surfaces 216A-B and/or surfaces 208A-B, 210A-B or other geometry of the surfaces in front of the user may be used to direct the user to positions that have been shown to be more ergonomic or provide better results of long term use, fatigue reduction, precise movements, etc. In still further aspects, the different surfaces 216A-B and/or surfaces 208A-B, 210A-B may be used to indicate a workspace size for applications like the EM ungrounded UIDS and/or indicate the width and/or depth of the workspace.

Figure 3:
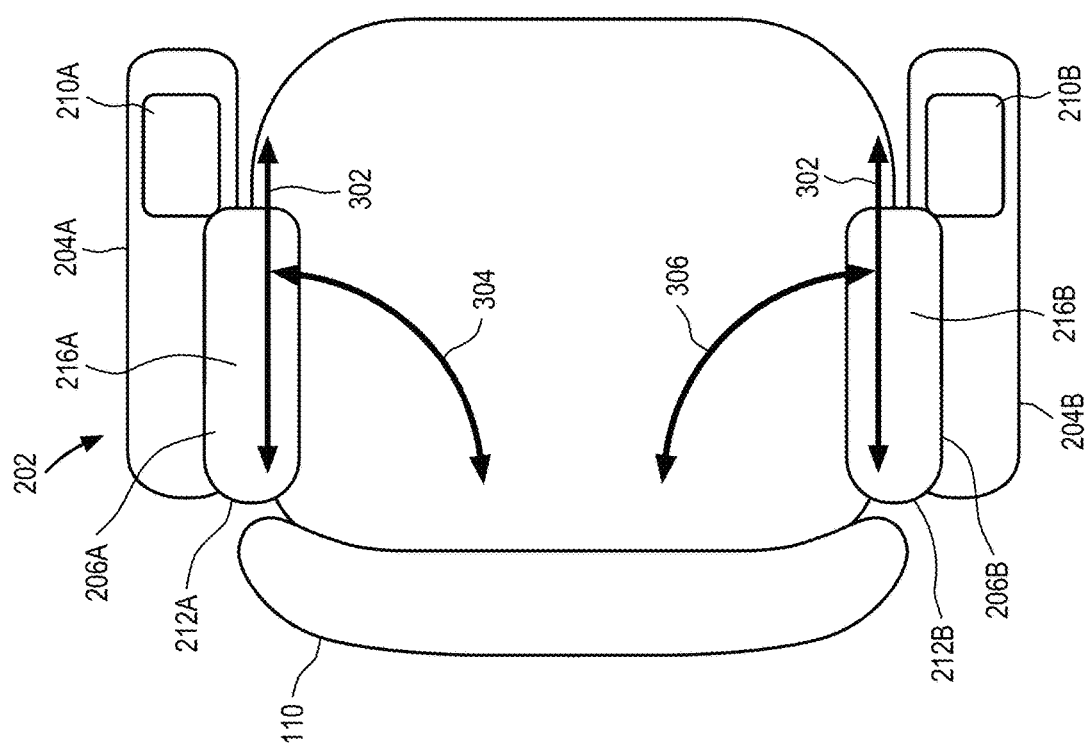
FIG. 3 illustrates a top plan view of an exemplary user console seat including an adjustable armrest system.

The adjustment of the adjustable armrest portion relative to the fixed armrest portion and different surface configurations that may be used to guide the adjustment will now be described in more detail in reference to FIGS. 3-8. Representatively, FIG. 3 illustrates a top plan view of a seat 110 including an arm support system 202. As previously discussed, arm support system 202 includes left and right stationary or fixed armrest portions 204A-B and adjustable armrest portions 206A-B movably coupled to the portions 204A-B. As can be seen from FIG. 3, the adjustable armrest portions 206A-B can be translated linearly as illustrated by arrows 302, or rotated as illustrated by arrows 304, 306, relative to fixed armrest portions 204A-B. The linear adjustment in a direction parallel to arrow 302 may be used to slide the adjustable armrest portions 206A-B between linearly stowed (or stored) and linearly deployed (or extended) positions and/or toward/away from a user seated in the seat 110. The rotational adjustment along arrows 304, 306 may be used to also move the adjustable armrest portion 206A-B between rotationally stowed (or stored) and rotationally deployed positions and/or in front of, or away from, a user seated in seat 110. The stowed (or stored) position should be understood as referring to a position of the adjustable armrest portion 206A-B when the adjustable armrest portion 206A-B is not in use (e.g., the surgeon is not using a UID to perform a surgical procedure from the console). The deployed position should be understood as referring to a position of the adjustable armrest portion 206A-B other than the stowed position (e.g., a position when the surgeon is preparing to use, or is using, the UID to perform a surgical procedure from the console).

Figure 4:
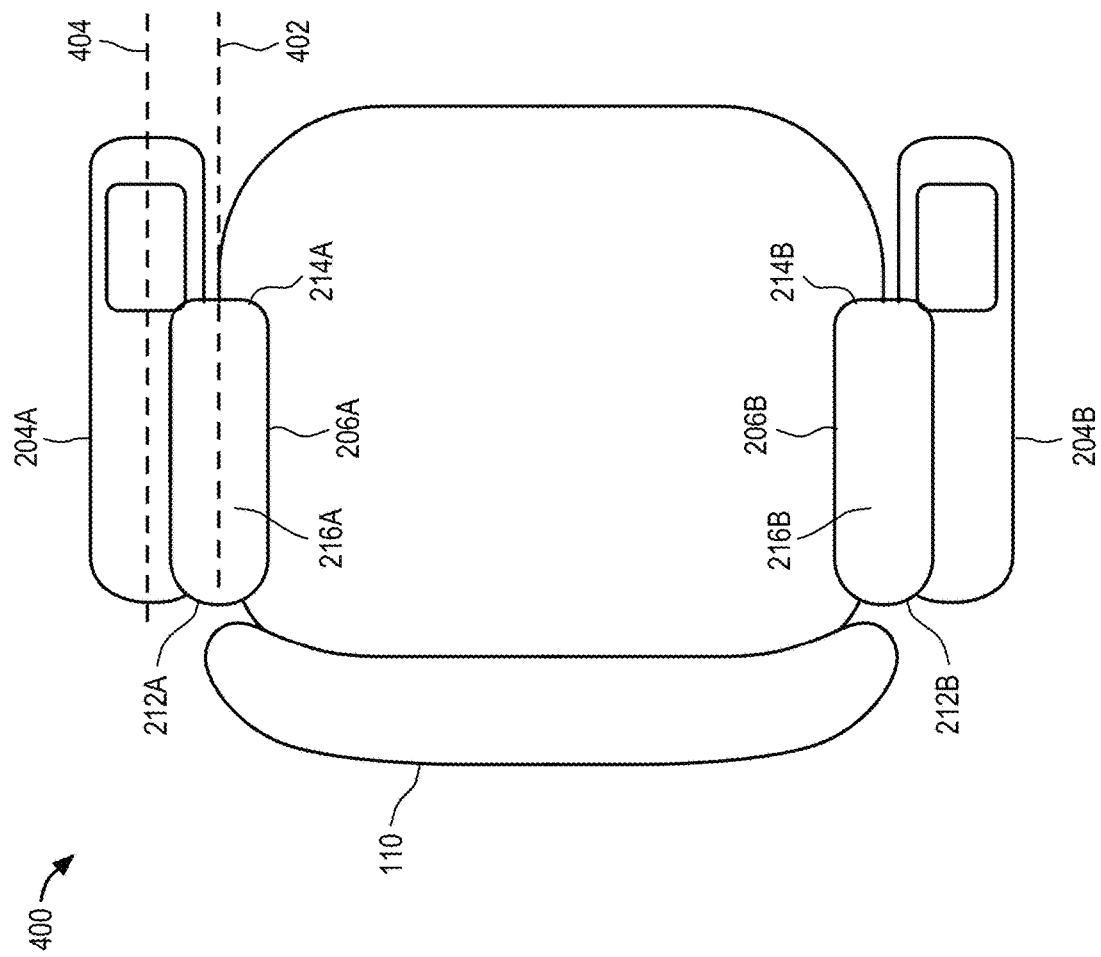
FIG. 4 illustrates a top plan view of an exemplary user console seat including an adjustable armrest system.
Figure 5:
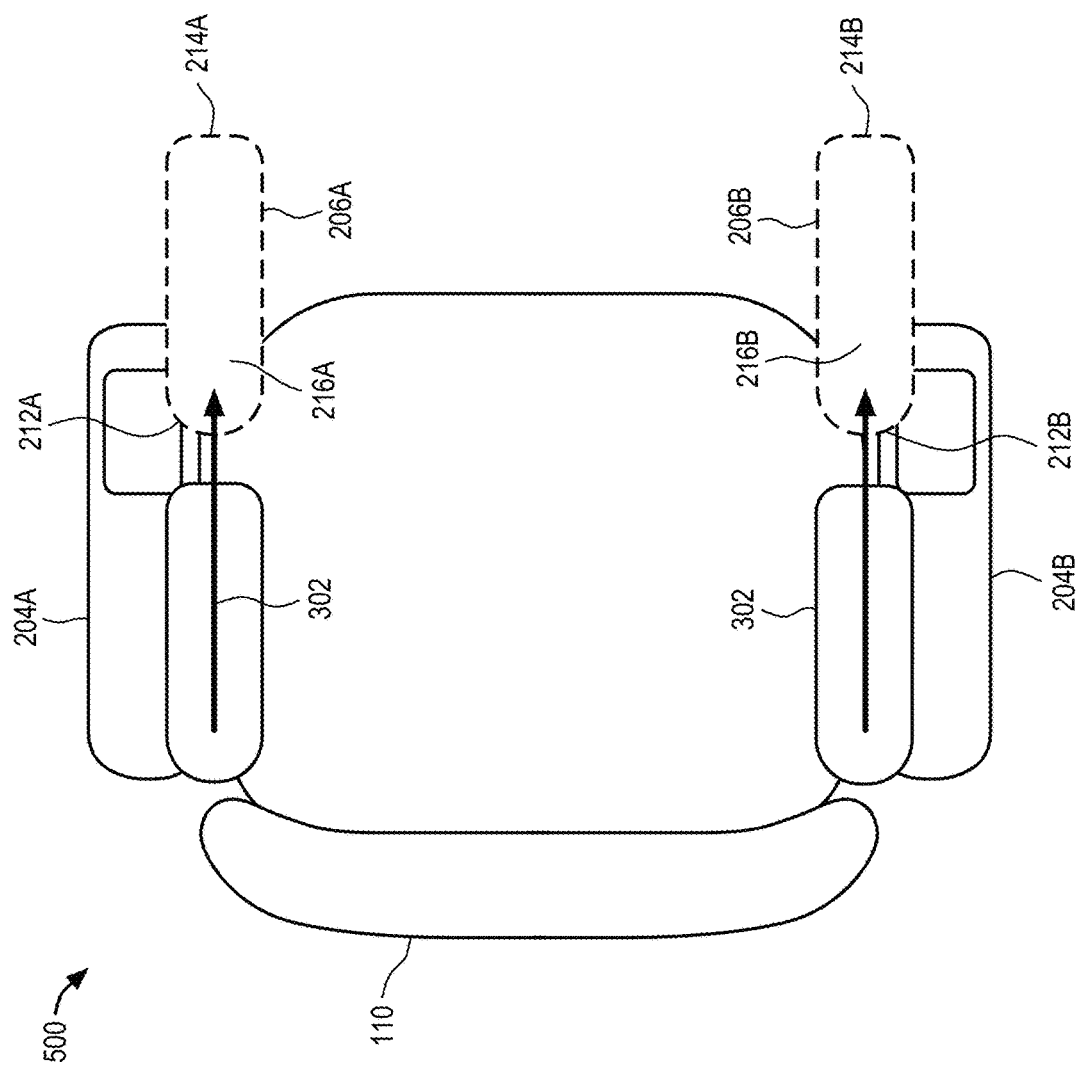
FIG. 5 illustrates a top plan view of an exemplary user console seat including an adjustable armrest system.

Representatively, when not in use, the adjustable armrest portion 206A-B may be in a linearly stowed or storage position as illustrated in FIGS. 3-4. In this stowed or storage position 400, the adjustable armrest portion 206A-B and associated work surface 216A-B are oriented parallel to, and considered proximal to, the fixed armrest portion 204A-B. For example, the proximal end 212A-B of the adjustable armrest portion 206A-B is aligned with the proximal end of the fixed armrest portion 204A-B. In addition, it can be seen that the length dimension, or longitudinal axis 402, of the adjustable armrest portion 206A-B and work surface 216A-B is parallel to the length dimension, or longitudinal axis 404, of the fixed armrest portion 204A-B. In the linearly deployed position 500 shown in FIG. 5, on the other hand, the adjustable armrest portion 206A-B moves linearly (or translates) from the storage position in a forward direction illustrated by arrow 302 to a position farther away from the back of the seat (along the longitudinal axis). In the linearly deployed position 500, the distal end 214A-B of the adjustable armrest portion 206A-B and work surface 216A-B may extend past (or distal to) the distal end of the fixed armrest portion 204A-B. In this aspect, in the deployed position, the adjustable armrest portion 206A-B and/or work surface 216A-B may be considered distal to the fixed armrest portion 204A-B. It should be understood, however, that FIG. 5 illustrates one exemplary linearly deployed position. The linearly deployed position may vary and include any position of the adjustable armrest portion 206A-B and work surface 216A-B that is between the stowed position 400 of FIG. 4 and the deployed position 500 of FIG. 5. For example, depending on the size of the user or particular operation being performed, the adjustable armrest portion 206A-B and work surface 216A-B could be closer to the back of the seat 110 in the linearly deployed position than position 500 shown in FIG. 5.

Figure 6:
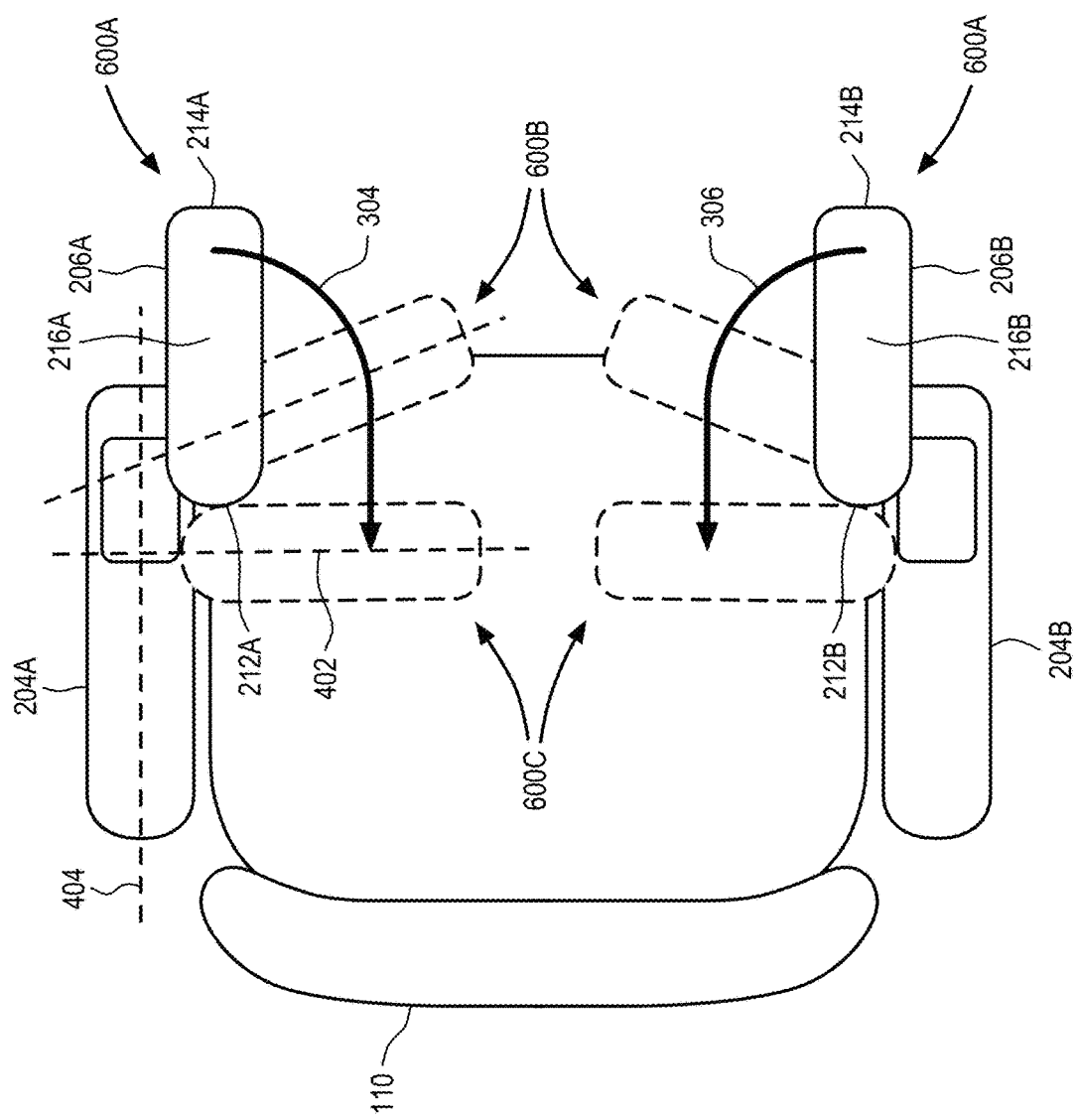
FIG. 6 illustrates a top plan view of an exemplary user console seat including an adjustable armrest system.

FIG. 6 illustrates the rotational adjustment of the adjustable armrest portion 206A-B from a rotationally stored position to different rotationally deployed positions. Representatively, as illustrated in FIG. 6, the adjustable armrest portion 206A-B may rotate or pivot as illustrated by arrows 304, 306 between positions 600A, 600B and 600C. In some aspects, position 600A may be considered a rotationally stored position 600A because there has been no rotational adjustment (e.g., movement along arrows 304, 306). It is noted that position 600A may correspond to the linearly deployed position 500 previously discussed in reference to FIG. 5. In the rotationally stored position 600A, the adjustable armrest portion 206A-B and work surface 216A-B may be parallel to the fixed armrest portion 204A-B (e.g., axis 402 of the adjustable armrest portion is parallel to axis 404 of the fixed armrest portion). Positions 600B and 600C may be considered rotationally deployed positions because adjustable armrest portion 206A-B and the work surface 216A-B is rotated along arrows 304, 306 to a position that is at an angle to the fixed armrest portion 204A-B. Representatively, in the rotationally deployed positions 600B-C, the length dimension or longitudinal axis 402 of the adjustable armrest portion 206A-B and work surface 216A-B is at an angle to the length dimension or longitudinal axis 404 of the fixed armrest portion 204A-B. For example, the adjustable armrest portion 206A-B may be rotated within an angle of 90 degrees or less to the fixed armrest portion 204A-B. It can be seen from FIG. 6 that in the rotationally deployed positions 600B-C, the adjustable armrest portion 206A-B would be arranged in front of a surgeon seated in seat 110 so that the user can use the work surface 216A-B to support their forearm, wrist or any other portion of their arm to, for example reduce fatigue, while operating the UID.

It should further be understood that while FIGS. 4-6 show both the left adjustable armrest portion 206A and right adjustable armrest portion 206B in stowed or deployed positions at the same time, the linear and rotational movements of the left adjustable armrest portion 206A and the right adjustable armrest portion 206B are independent from one another and are not necessarily in the same position. Rather, the left adjustable armrest portion 206A and the right adjustable armrest portion 206B may be adjusted to different positions so that one is in one stowed position and another is in another stowed position or one of the deployed positions. For example, both the left and right adjustable armrest portion 206A-B may be in the linearly stowed position 400 of FIG. 4 when not in use, then adjusted by the user to different stowed and/or deployed positions (e.g., any one or more of positions 400, 500, 600B, 600C) depending on the size of the user and/or operation to be performed.

Figure 7:
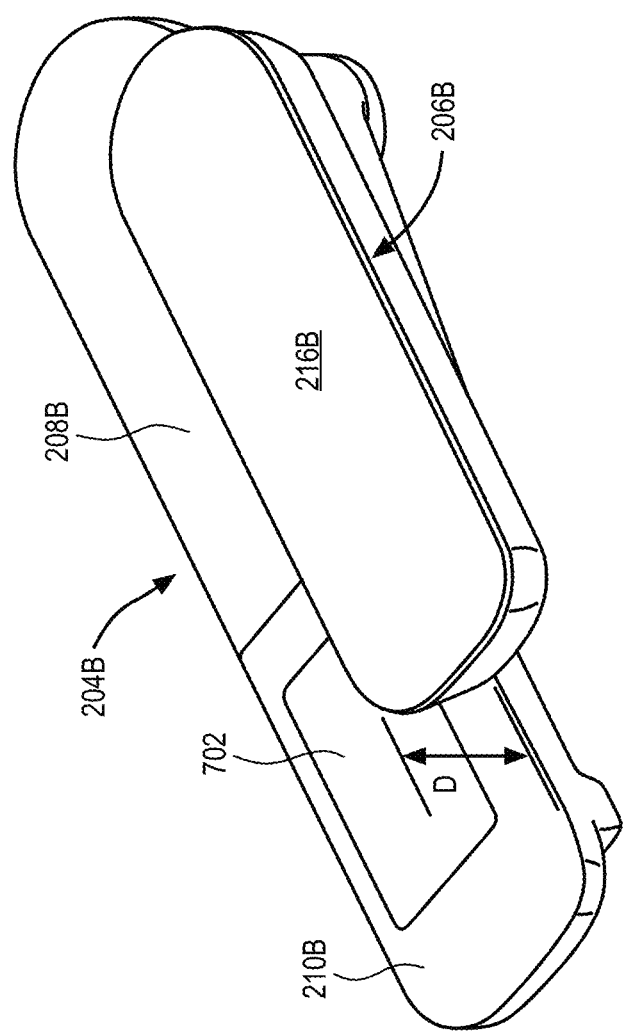
FIG. 7 illustrates a perspective view of an exemplary adjustable armrest system.
Figure 8:
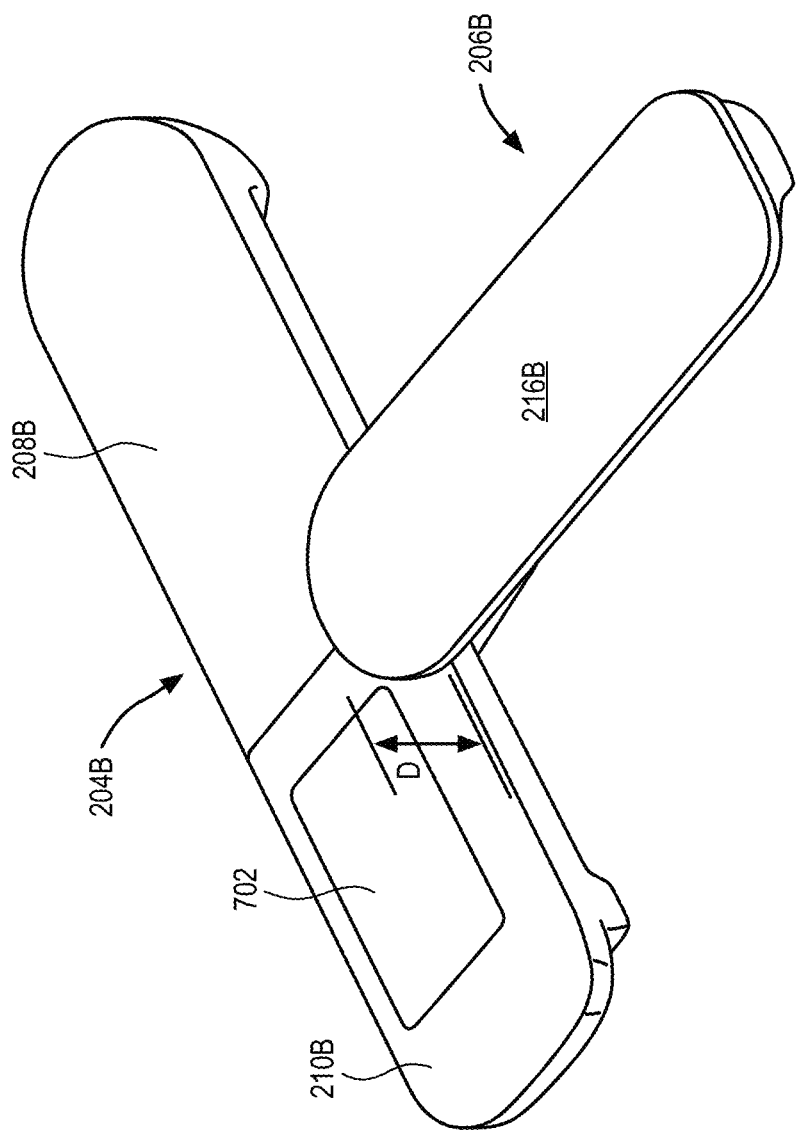
FIG. 8 illustrates a perspective view of an exemplary adjustable armrest system.

Moreover, as previously discussed and as illustrated by FIGS. 7-8, the fixed armrest portion 204A-B and adjustable armrest portion 206A-B may have distinct surface areas that can be used to assist the user with armrest positioning. Representatively, the right adjustable armrest portion 206B is shown having work surface 216B out-of-plane relative to the support surface 208B of the fixed armrest portion 204B. For example, as illustrated by FIG. 7, work surface 216B (or a plane defined by work surface 216B) is at a distance (D) above the support surface 208B (or a plane defined by support surface 208B). In addition, the fixed armrest portion 204B includes input surface 210B at the distal end. The input surface 210B could be, for example, a touch pad 702 or the like that the user can use to control one or more operations of the surgical robotic system. Each of these different surfaces 208B, 210B 216B can be readily distinguishable by touch by the user so they can provide guides to the user and, in some cases, the desired orientation of the armrest portions relative to one another can be achieved, without the user having to look away from the display toward the armrest system. For example, as previously discussed, the adjustable armrest portion 204B, and particularly the work surface 216B, may be used as the work/support surface in front of the user when positioned in the seat 110. For example, work surface 216B may be used to support the user's forearms/elbows/wrists during teleoperation with the ungrounded UIDs. In addition, the adjustable armrest portion 204B may be used to set the size of the workspace and direct the user to position their arms in preferred positions for teleoperation. For example, the width/gap between the adjustable arm portion 206A-B or other geometry of the work surface 216B in front of the user may be used to direct the user to positions that have been shown to be more ergonomic or provide better results for long term use, fatigue reduction, precise movements etc. In addition, the support surface 208B (and support surface 208A) of the fixed armrest portion 204A-B may be used to indicate the workspace size for the ungrounded UIDs. The adjustable arm portion 206A-B and work surface 216A-B can also be used to set the support surface and/or indicate either the width or depth of the workspace. The deployable linear/rotatable system attached to the seat as described herein allows for the potential of an open front to the system to allow the surgeon to be engaged with and have direct sight forward of his/her seating position. In addition, it should be understood that while the left adjustable armrest portion 206B and left fixed armrest portion 204B are shown and described in reference to FIGS. 7-8, the description should be understood as applying to the right armrest portions 204A and 206A.

Figure 9:
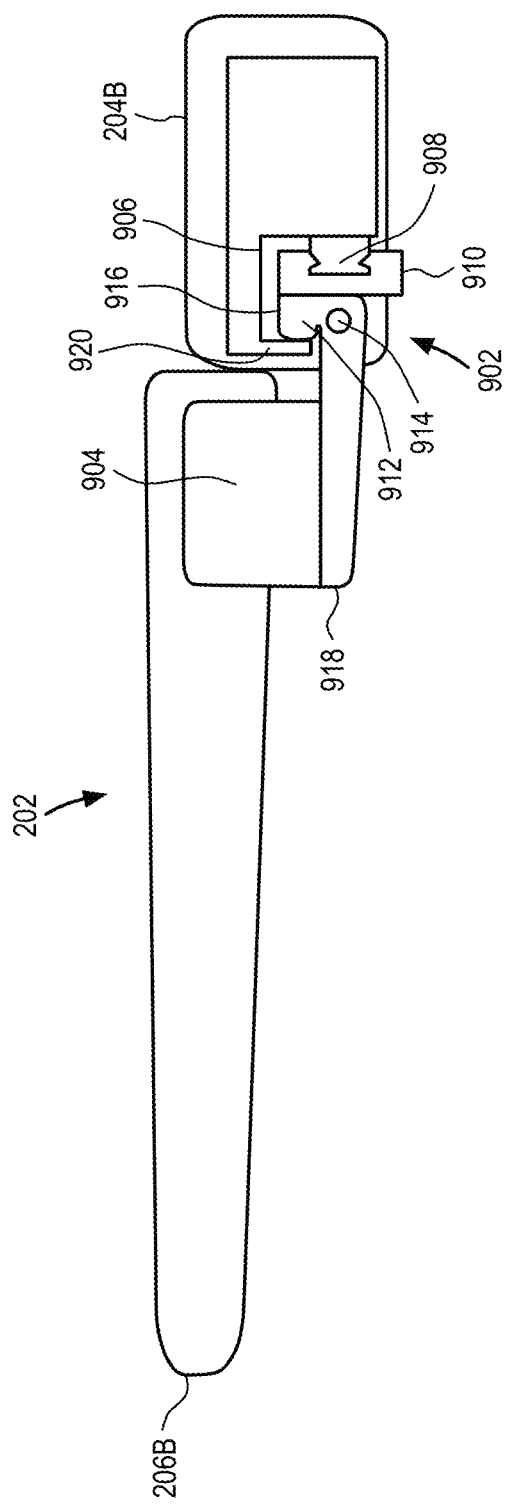
FIG. 9 illustrates a side cross-sectional view of an exemplary adjustable armrest system.
Figure 10:
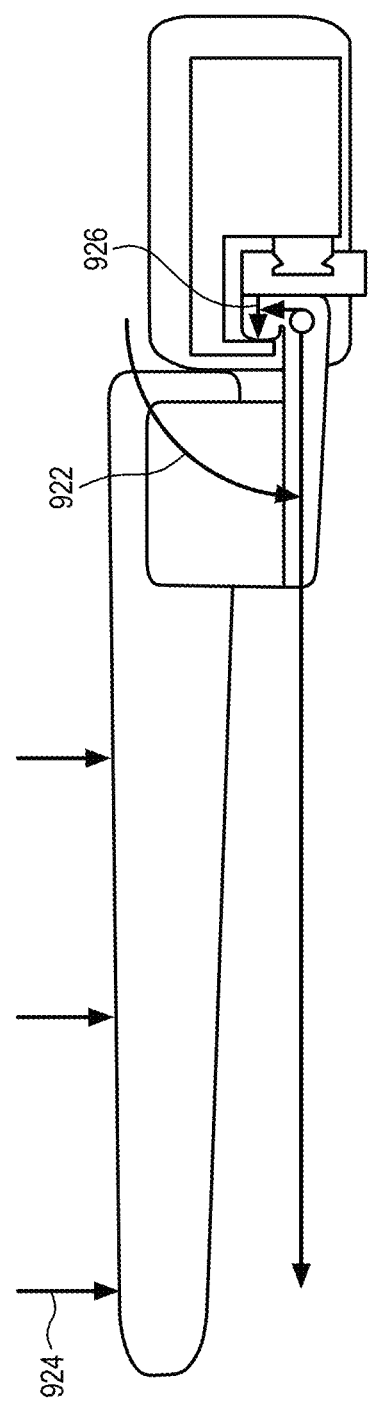
FIG. 10 illustrates a side cross-sectional view of an exemplary adjustable armrest system.
Figure 11:
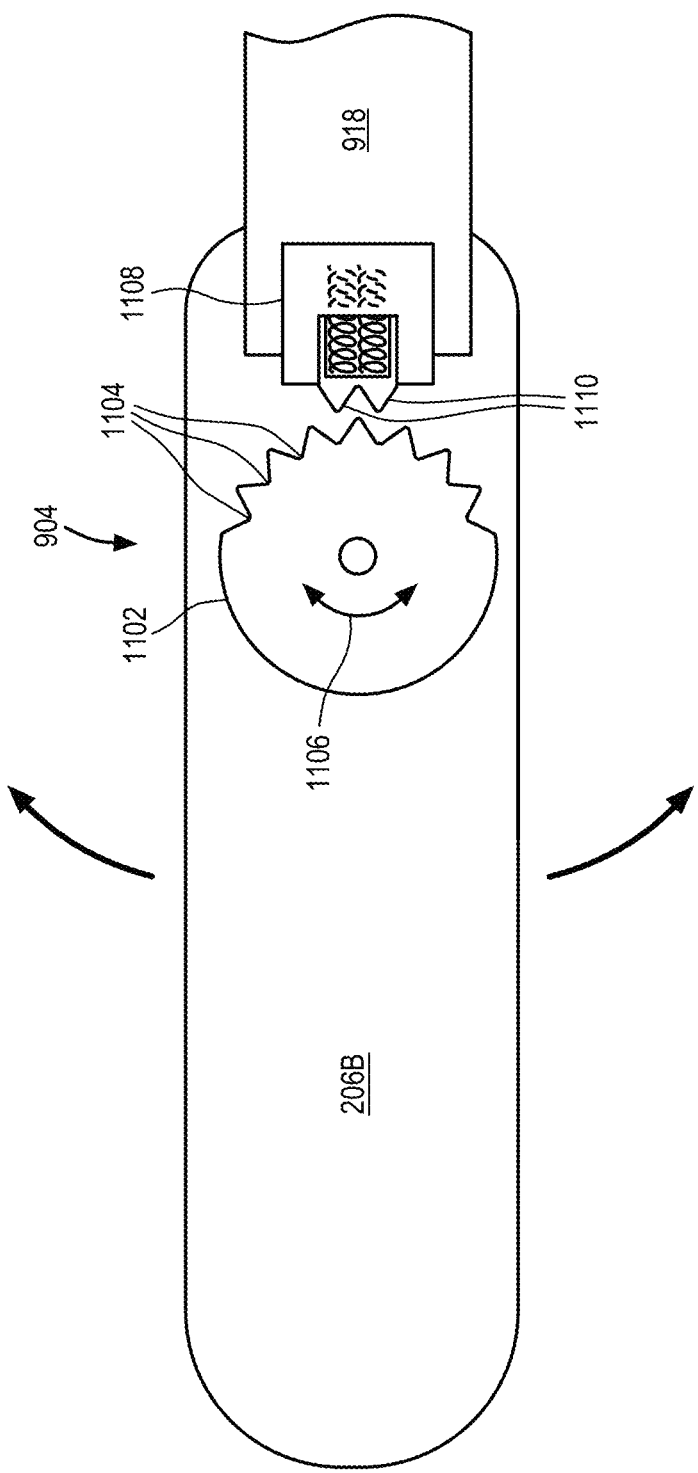
FIG. 11 illustrates a bottom plan view of an exemplary adjustable armrest system.

As will now be described in reference to FIGS. 9-11, the arm support system may further include a locking mechanism to lock or otherwise control the positioning and/or repositioning of the adjustable armrest portion relative to the fixed armrest portion. Representatively, FIGS. 9-10 illustrate an end cross-sectional view of the arm support system including a linear and rotational locking mechanism. FIG. 11 illustrates a magnified top view of the rotational locking mechanism. Returning now to FIGS. 9-10, it can be seen from this view that the linear locking mechanism 902 includes a bracket or other similarly rigid structure that forms an interior channel 906 within the fixed arm rest portion 204B. Along one side of the interior channel 906 is a rail 908 along which a linear slide 910 of the adjustable armrest portion 206B slides to allow for linear movement, as previously discussed. The linear slide 910 may be, for example, a C shaped bracket dimensioned to receive rail 908 within a recessed region and slide linearly along the rail 908. The other side of the linear slide 910 may be attached to a locking member 912. The locking member 912 may include an engagement portion 916 and a support portion 918 that extends from the engagement portion 916. The engagement portion 916 is a protruding structure that is adjacent the linear slide 910 along one side and is positioned within the interior channel 906 along with the linear slide 910. The other side of the engagement portion 916 faces an outer braking wall 920 of channel 906 and is connected to the support portion 918. The support portion 918 extends outside of the channel 906 and is connected to the adjustable armrest portion 206B by the rotational locking mechanism 904. Accordingly, when linearly adjusting the position of the adjustable armrest portion 206B, the linear slide 910 (along with the locking member 912, rotational locking mechanism 904 and adjustable armrest portion 206B) slides linearly relative to the linear rail 908 and channel 906 of the fixed armrest portion 204B.

To achieve linear locking (e.g. prevent movement in the linear direction), the locking member 912 is further pivotally coupled to the linear slide 910 at pivot point 914. This allows locking member 912 to pivot downward in the direction of arrow 922 upon application of a downward force 924 on the adjustable armrest portion 206B as shown in FIG. 10. When locking member 912 pivots downward, the engagement portion 916 moves in the direction illustrated by arrow 926 and engages with the inner surface of the braking wall 920 of channel 906. The frictional forces created between the surfaces of engagement portion 916 and braking wall 920 upon application of the downward pressure prevents linear translation of the linear slide 910 relative to the linear rail 908. This, in turn, locks the adjustable armrest portion 206B at whatever linear position it may be in at the time the downward force is applied (e.g., positions 400, 500, etc.) In addition, it should be understood that the pressing of the engagement portion 916 against the braking wall 920 amplifies downward force on the adjustable armrest portion 206B, which helps lock out the linear movement when the armrest is in use. In addition, it should be understood that while the left adjustable armrest portion 206B and left fixed armrest portion 204B are shown and described in reference to FIGS. 9-10, the description should be understood as applying to the right armrest portions 204A and 206A.

In some aspects, the downward pressure 924 may be caused by the user resting their arm on the adjustable armrest portion 206B at any point while the user is seated in the chair. In this aspect, the linear locking/brake mechanism can be automatically engaged when the user rests their arm on the adjustable armrest portion 206B without any additional or extra steps and/or operations to lock the adjustable armrest portion 206B in the desired linear position (e.g, a deployed position). Prior to application of the force or upon removal of the force such as by lifting the user's arm, the adjustable armrest portion 206B is free to move forward and to adjust for user size and positional preference for surgical tasks. In this aspect, the armrest system is easily positionable in the most ergonomic and useful position with minimal effort in perioperative situations with minimal effort but once in position, the support system is stable while the surgeon moves the UIDs. In addition, when the adjustable armrest support is deployed in front of the user, it is easily disengaged from the locked position (e.g., by lifting the user's arm) for egress in case of emergency during a surgical procedure. This configuration may also enable overload protection for the linear locking mechanism by translating the moment load into a normal load that can prevent damage to the mechanism.

It should further be understood that although one particular linear locking mechanism is shown in FIGS. 9-10, the user load may be translated to the linear locking mechanism using a variety of geometries, arm levels, locations, materials, etc. other than what is shown in the drawings. In addition, the linear slide may also be positioned in alternative arrangements or shared with multiple linear slides.

Referring now in more detail to the rotational locking mechanism 904, it can be seen from FIG. 11 that the rotational locking mechanism 904 includes a cam 1102 having notches or grooves 1104 that may be engaged by detents 1110 to lock, control or otherwise modify a force required for rotational adjustment of the adjustable armrest portion 206B relative to the fixed armrest portion (not shown). Representatively, cam 1102 may be attached to the adjustable armrest portion 206B. In this aspect, rotation of the adjustable armrest portion 206B may also rotate the cam 1102 as illustrated by arrow 1106. The detents 1110 may be coupled to a block 1108 attached to the support portion 918 of the locking member. As previously discussed, the support portion 918 may be mounted to a bottom side of the adjustable armrest portion 206B and couples the adjustable armrest portion 206B to the fixed armrest portion 204B. The support portion 918 slides linearly relative to the fixed armrest portion 204B to allow for linear movement of the adjustable armrest portion 206B relative to the fixed armrest portion 204B, however, does not rotate along with the adjustable armrest portion 206B. Accordingly, rotation of the adjustable armrest portion 206B and the cam 1102 as shown by arrow 1106 rotates the cam 1102 past the detents 1110 coupled to the support portion 918. In some aspects, the detents 1110 may be spring loaded. For example, the detents 1110 may be coupled to a spring that biases the detents toward the grooves. The cam 1102 and detents 1110 allow for a tune-able holding force and specific angles of adjustment without electronic inputs or extra steps by the user to set the position. This design allows for the holding force and feel to be adjusted by changing the cam geometry or the spring force and size of the detent. For example, in one aspect, the rotational locking mechanism 904 may have the following positions: stored at 0 degrees with two detents engaged (double holding force) and alternating adjustment angles at 30-90 degrees every 10 degrees with one detent engaged in each position. In other words, depending on the resistance desired, the detents can be configured to engage one groove (single effect) or two grooves (double effect) at the same time. When one detent is engaged, it is easier for the user to move the arm (e.g., less rotational force input), and if two detents are engaged it is harder to move the arm (e.g., more rotational force input). The detents 1110 and grooves 1104 may be offset so the user can selectively engage amount of grooves to decrease/increase resistance to rotation. For example, there are some arm positions where the user does not want to have to input a large amount of force, for example in the beginning while they are setting up for a procedure. As the arm rotates out more, however, closer to the 90 degree working position, the user may want to have higher force or resistance to rotation. In addition, in some aspects, detents 1110 may be radial to the axis of rotation as shown. In other aspects, detents 1110 may also be oriented parallel to the axis with grooves 1104 on a surface perpendicular to the axis. In addition, the rotational locking mechanism 904 may provide haptic feedback to the user as the arm is rotated and the detents 1110 and grooves 1104 engage/disengage (e.g., a clicking feeling).

Figure 12:
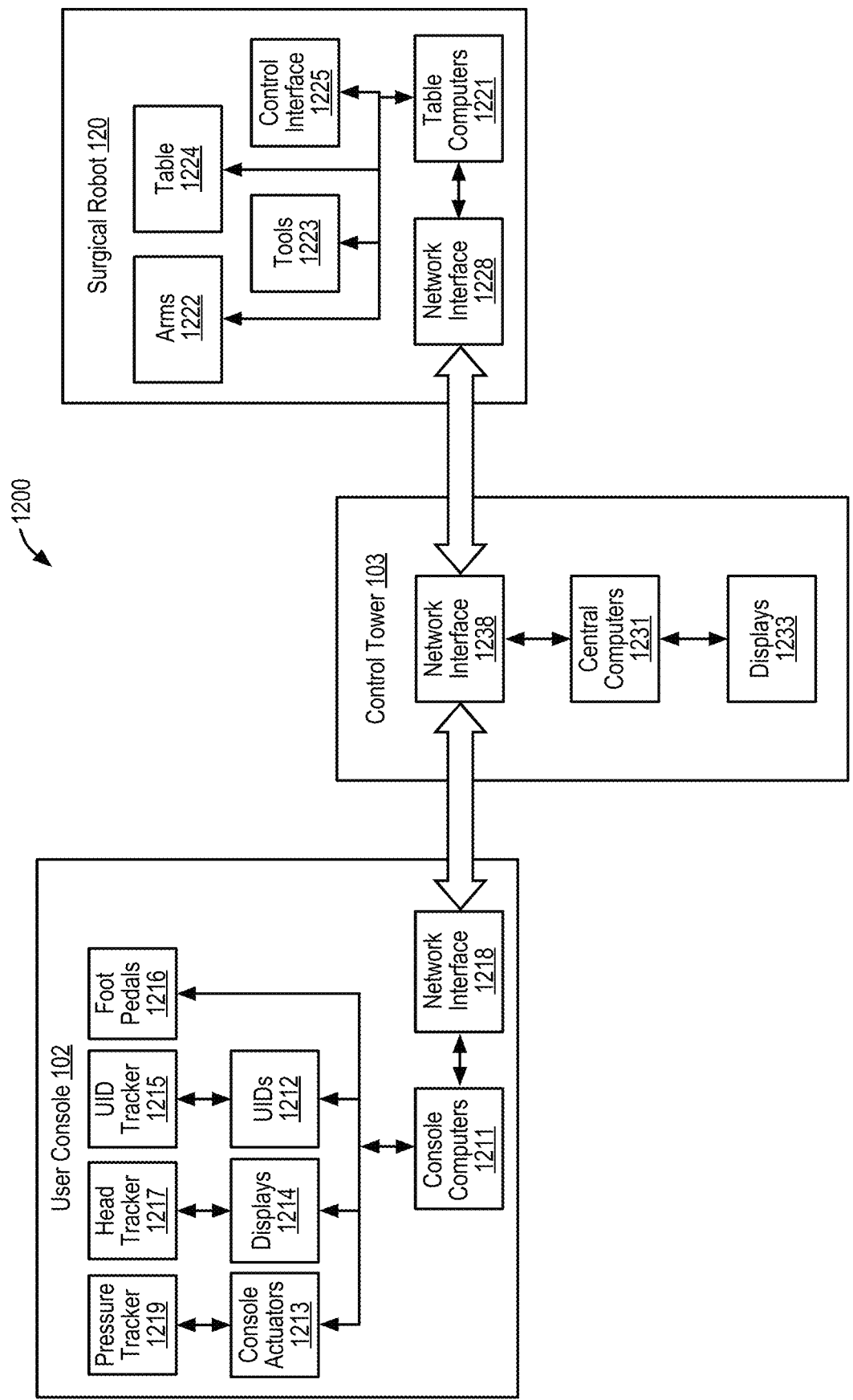
FIG. 12 is a block diagram of a computer portion of a user console.

FIG. 12 is a block diagram of a computer portion of a surgical robotic system, which is operable to implement the previously discussed operations, in accordance with an embodiment. The exemplary surgical robotic system 1200 may include a user console 102, a surgical robot 120, and a control tower 103. The surgical robotic system 1200 may include other or additional hardware components; thus, the diagram is provided by way of example and not a limitation to the system architecture.

As described above, the user console 102 may include console computers 1211, one or more UIDs 1212, console actuators 1213, displays 1214, foot pedals 1216, console computers 1211 and a network interface 1218. In addition, user console 102 may include a number of components, for example, a UID tracker(s) 1215, a display tracker(s) 1217 and a console tracker(s) 1219, for detecting various surgical conditions required for operation of the system (e.g., UID orientation, orientation of the surgeon relative to the display, orientation the console seat, etc). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1213 based on user input or stored configurations by the console computers 1211. The user may perform robot-assisted surgeries by controlling the surgical robot 120 using one or more master UIDs 1212 and foot pedals 1216. Positions and orientations of the UIDs 1212 are continuously tracked by the UID tracker 1215, and status changes are recorded by the console computers 1211 as user input and dispatched to the control tower 103 via the network interface 1218. Real-time surgical video of patient anatomy, instrumentation, and relevant software apps can be presented to the user on the high resolution 3D displays 1214 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 12, the control tower 103 may include central computers 1231 including at least a visualization computer, a control computer, and an auxiliary computer, various displays 1233 including a team display and a nurse display, and a network interface 1218 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an operating table 1224 with a plurality of integrated robotic arms 1222 that can be positioned over the target patient anatomy. A suite of compatible tools 1223 can be attached to or detached from the distal ends of the arms 1222, enabling the surgeon to perform various surgical procedures. The surgical robot 120 may also comprise control interface 1225 for manual or automated control of the arms 1222, table 1224, and tools 1223. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1222 includes four arms mounted on both sides of the operating table 1224, with two arms on each side. For certain surgical procedures, an arm mounted on one side of the table can be positioned on the other side of the table by stretching out and crossing over under the table and arms mounted on the other side, resulting in a total of three arms positioned on the same side of the table 1224. The surgical tool can also comprise table computers 1221 and a network interface 1218, which can place the surgical robot 120 in communication with the control tower 103.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. An adjustable arm support for a surgical robotic system, the arm support comprising:
   a fixed armrest portion that is fixedly coupled to a console seat of the surgical robotic system, the fixed armrest portion having an input surface defining a first horizontal plane and operable to receive an input from a user; and
   an adjustable armrest portion that is coupled in a laterally offset position to the fixed armrest portion, the adjustable armrest portion having a work surface defining a second horizontal plane spaced at a distance and parallel to the first horizontal plane, and the adjustable armrest portion is operable to be adjusted relative to the fixed armrest portion linearly along a first axis and rotatably about a second axis that is perpendicular to the first axis.

2. The arm support of claim 1 wherein the adjustable armrest portion is shorter than the fixed armrest portion and linearly adjusted between a stored position and a deployed position.

3. The arm support of claim 2 wherein the adjustable armrest portion comprises a linear slide that translates along a linear rail coupled to the fixed armrest portion to allow for adjustment of the adjustable armrest portion between the stored position and the deployed position.

4. The arm support of claim 2 wherein the adjustable armrest portion comprises a proximal end and a distal end, and the distal end is adjacent the fixed armrest portion in the stored position and distal to the fixed armrest portion in the deployed position.

5. The arm support of claim 1 wherein the second axis is a vertical axis and the adjustable armrest portion is rotatably adjusted between a stored position and a deployed position.

6. The arm support of claim 5 wherein the adjustable armrest portion runs parallel to the fixed armrest portion in the stored position and is at an angle to the fixed armrest portion in the deployed position.

7. The arm support of claim 1 wherein the adjustable armrest portion remains within the second horizontal plane during both the linear and rotatable adjustment.

8. The arm support of claim 1 further comprising a linear locking mechanism that prevents a linear adjustment of the adjustable armrest portion relative to the fixed armrest portion upon application of a downward force to the adjustable armrest portion.

9. The arm support of claim 1 further comprising a rotational locking mechanism for adjusting a force required for a rotational adjustment of the adjustable armrest portion relative to the fixed armrest portion.

10. The arm support of claim 9 wherein the rotational locking mechanism comprises a cam having at least one notch and at least one detent that engages with the at least one notch to increase the force required for rotational adjustment.

11. An adjustable arm support for a surgical robotic system, the arm support comprising:
    an armrest base that is fixedly coupled to a user console seat of the surgical robotic system;

a deployment arm coupled to the armrest base at a laterally offset position, the deployment arm is operable to be linearly or rotatably adjusted relative to the armrest base between a stored position and a deployed position; and a locking mechanism operable to lock the deployment arm in the deployed position by preventing a linear or rotatable adjustment of the deployment arm relative to the armrest base, and wherein linear adjustment of the deployment arm is prevented upon application of a downward force to the deployment arm or rotatable adjustment of the deployment arm is prevented by adjusting a force required for rotatable adjustment of the deployment arm.

12. The adjustable arm support of claim 11 wherein in the stored position, the deployment arm is parallel to the armrest base.

13. The adjustable arm support of claim 11 wherein in the deployed position, the deployment arm is at an angle up to 90 degrees relative to the armrest base.

14. The adjustable arm support of claim 11 wherein the locking mechanism comprises a linear locking mechanism that prevents the linear adjustment of the deployment arm upon application of the downward force to the deployment arm.

15. The adjustable arm support of claim 14 wherein the linear locking mechanism comprises a channel within the armrest base that engages with a sliding member of the deployment arm upon application of the downward force to the deployment arm to prevent the linear adjustment.

16. The adjustable arm support of claim 11 wherein the locking mechanism comprises a rotational locking mechanism that adjusts the force required for a rotatable adjustment of the deployment arm.

17. The adjustable arm support of claim 16 wherein the rotational locking mechanism comprises a cam with at least one notch coupled to the deployment arm and at least one detent coupled to a support portion extending from the armrest base, and wherein a rotatable adjustment of the deployment arm causes a rotation of the cam relative to the at least one detent allowing the at least one detent to engage the at least one notch to increase the force required for rotatable adjustment of the deployment arm.

18. The adjustable arm support of claim 17 wherein the cam comprises at least two notches and at least two detents are coupled to the support portion, and engaging the at least two detents with the at least two notches increases a force required to rotate the deployment arm.

19. The adjustable arm support of claim 17 wherein the at least one detent is coupled to a spring that biases the at least one detent toward the at least one notch.

20. The adjustable arm support of claim 17 wherein the rotational locking mechanism provides a haptic feedback to a user when the deployment arm is rotatably adjusted relative to the armrest base between the stored position and the deployed position.

* * * * *